US010690662B2

(12) United States Patent
Elangovan et al.

(10) Patent No.: US 10,690,662 B2
(45) Date of Patent: Jun. 23, 2020

(54) MAGNETIC CAPTURING OF RARE CELLS

(71) Applicant: INDIAN INSTITUTE OF TECHNOLOGY DELHI, New Delhi (IN)

(72) Inventors: Ravikrishnan Elangovan, New Delhi (IN); Vivekanandan Perumal, New Delhi (IN); Shalini Gupta, New Delhi (IN); Saurabh Singh, New Delhi (IN)

(73) Assignee: INDIAN INSTITUTE OF TECHNOLOGY DELHI, New Delhi (IN)

( * ) Notice: Subject to any disclaimer, the term of this patent is extended or adjusted under 35 U.S.C. 154(b) by 423 days.

(21) Appl. No.: 15/531,401

(22) PCT Filed: Nov. 6, 2015

(86) PCT No.: PCT/IN2015/050155
§ 371 (c)(1),
(2) Date: May 26, 2017

(87) PCT Pub. No.: WO2016/084102
PCT Pub. Date: Jun. 2, 2016

(65) Prior Publication Data
US 2017/0328893 A1 Nov. 16, 2017

(30) Foreign Application Priority Data
Nov. 28, 2014 (IN) .............. 3465/DEL/2014

(51) Int. Cl.
*G01N 33/543* (2006.01)
*G01N 33/574* (2006.01)
*B01L 3/00* (2006.01)

(52) U.S. Cl.
CPC .. *G01N 33/54326* (2013.01); *B01L 3/502715* (2013.01); *B01L 3/502761* (2013.01);
(Continued)

(58) Field of Classification Search
CPC ....... G01N 33/54326; G01N 33/54366; G01N 33/574; B01L 3/502715; B01L 3/502761;
(Continued)

(56) References Cited

U.S. PATENT DOCUMENTS 9,421,555 B2 * 8/2016 Lee ................... B03C 1/032
2012/0149021 A1 * 6/2012 Yung ................ B03C 1/01
435/6.12

FOREIGN PATENT DOCUMENTS

EP       2579988 A2    4/2013
WO    2010121315 A1   10/2010
WO    2013078332 A1    5/2013

OTHER PUBLICATIONS

International Search Report and Written Opinion for PCT App No. PCT/IN2015/050155 dated Mar. 1, 2016, 8 pgs.

* cited by examiner

*Primary Examiner* — Sally A Merkling
(74) *Attorney, Agent, or Firm* — Procopio, Cory, Hargreaves & Savitch LLP

(57) ABSTRACT

The subject matter discloses systems and methods for magnetic capturing of rare cells from a liquid sample. The system includes a capture chip (104) having a longitudinal channel (208) comprising a first part (304) and a second part (306). The capture chip (104) has a capture well (302) near an end of the second part (306) closer to an interfacing region between the first part (304) and the second part (306). The system includes a first set (126) of multiple rows of magnets for the magnetic capturing of the rare cells in the first part (304) of the longitudinal channel (208), where a first row (132) of the first set (126) of multiple rows has magnets that span a length of the first part (304) of the (Continued)

longitudinal channel (208) and each subsequent row of the first set (126) of multiple rows has one magnet less than a previous row.

17 Claims, 9 Drawing Sheets

(52) U.S. Cl.
CPC ..... *G01N 33/54366* (2013.01); *G01N 33/574* (2013.01); *B01L 2200/025* (2013.01); *B01L 2200/0647* (2013.01); *B01L 2300/0816* (2013.01); *B01L 2300/0877* (2013.01); *B01L 2300/0887* (2013.01); *B01L 2400/043* (2013.01)

(58) Field of Classification Search
CPC ..... B01L 2300/0877; B01L 2200/0647; B01L 2400/043; B01L 2300/0887; B01L 2300/0816; B01L 2200/025
See application file for complete search history.

MAGNETIC CAPTURING OF RARE CELLS

CROSS-REFERENCE TO RELATED APPLICATIONS

This application is a U.S. National Stage entry of PCT Application No. PCT/IN2015/050155, filed on Nov. 6, 2015, which claims priority to Indian Patent Application No. 3465/DEL/2014, filed Nov. 28, 2014, the contents of which are incorporated herein by reference.

TECHNICAL FIELD

The present subject matter relates, in general, to capturing of rare cells and particularly to magnetic capture of rare cells.

BACKGROUND

Rare cells refer to cells present in very low concentrations, typically at less than 1000 cells per milliliter of bio-sample. Rare cells include viruses, prokaryotes, proteins, and such, present in bio-samples. For instance, in case of circulating tumor cells, the concentrations can be as low as 1 cell in 7 ml. Such rare cells in bio-samples may have to be captured for removal of the rare cells from the bio-samples or for detection of rare cells.

BRIEF DESCRIPTION OF DRAWINGS

The features, aspects, and advantages of the subject matter will be better understood with regard to the following description, and accompanying figures. The use of the same reference number in different figures indicates similar or identical features and components.

DETAILED DESCRIPTION

Figure 1:
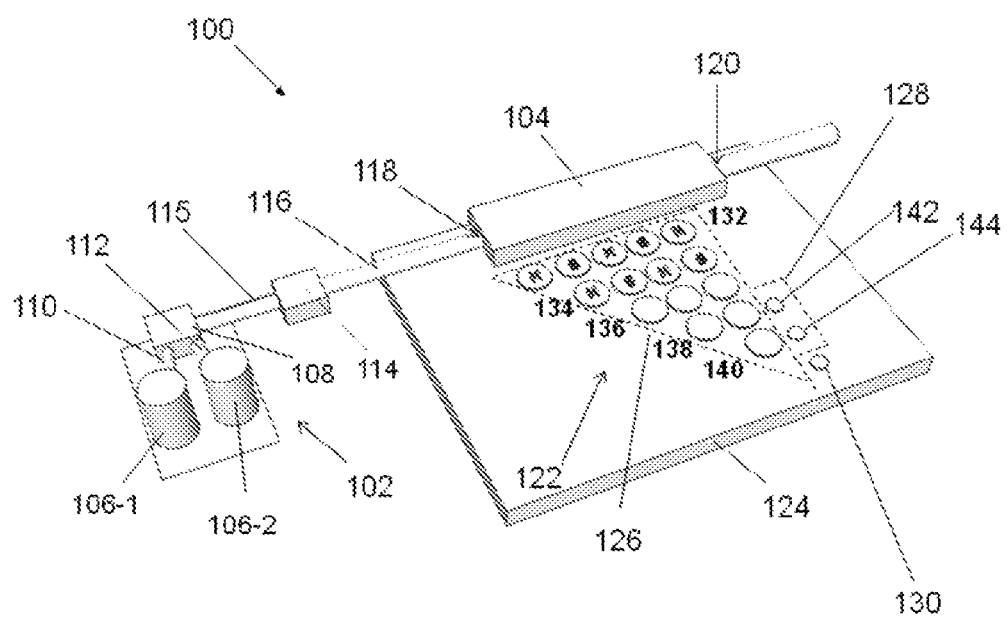
FIG. 1 illustrates a cell capturing system for magnetic capturing of rare cells from a liquid sample, in accordance with an implementation of the present subject matter.

The present subject matter disclosed herein, relates to capturing of rare cells, and methods and systems to magnetically capture rare cells within a small capturing region.

Rare cells are present at concentrations lesser than 1000 cells per milliliter of bio-sample. The capturing and the detection of rare cells in a bio-sample, for instance, a blood sample, is difficult due to the presence of a multitude of other cells, such as, the normal blood cells, along side the rare cells in the bio-sample.

The rare cells in a bio-sample are typically captured and detected based on immunomagnetic capture and fluorescence-based detection methodology, in which the rare cells are marked with magnetic and fluorescent particles. For this, the magnetic and fluorescent particles are conjugated with specific antibodies having high affinity towards the rare cells. The bio-sample is then incubated with the conjugated particles to form sandwich complexes of the magnetic particle, the rare cell and the fluorescent particle. The sandwich complexes are separated from the bio-sample to capture the rare cells. The separation is done by flowing the bio-sample over a region under the influence of an external magnetic field. The captured rare cells, or the sandwich complexes, are viewed under a fluorescent microscope to detect the rare cells. The fluorescent signal obtained based on the fluorescent particles attached with the captured rare cells is proportional to the concentration of the captured rare cells and can be used for quantification of the rare cells.

Typically, for imaging fluorescently labelled rare cells the fluorescent microscope with a high numerical aperture objective and 60× magnification is used. With such an objective lens, the area that can be viewed or imaged at an instant of time under the fluorescent microscope is of the order of 0.04 mm$^2$. However, with the conventional methodology, the rare cells, or the sandwich complexes, are captured in an area of the order of 100-1000 mm$^2$. Thus, the time taken to image or view the entire capture area to detect the captured rare cells is substantially large.

Further, since the rare cells are present in the bio-sample in a substantially low concentration, a large volume of bio-sample, for example 5 ml to 10 ml, is typically flowed for the purpose of capturing of the rare cells. In the conventional methodology, the bio-sample is flowed at a low flow rate in a range from 10 µl/min to 200 µl/min in order to capture sufficient number of rare cells for effective detection of the captured rare cells. Such slow flow rates are used when diameter of magnetic particle used is below 1000 nm. Due to this limitation on the flow rate and processing of a large volume of the bio-sample, the time taken for capturing of sufficient number of rare cells is substantially high.

The present subject matter describes methods and systems for magnetic capturing of rare cells from a liquid sample. The liquid sample herein may be understood as a bio-sample having rare cells. The rare cells in the liquid sample are conjugated at least with magnetic particles through a binding agent, for example, a specific antibody. The rare cells can also be conjugated with the fluorescent particles for the purpose of detection of captured rare cells. With the methods and the systems of the present subject matter, the rare cells can be magnetically captured within a substantially smaller area and with the liquid sample flowing at a substantially higher flow rate. The capturing of the rare cells in a substantially smaller area facilitates in reducing the time taken to view or image the capture area. This enables in faster detection of rare cells once captured in the capture area in comparison to the time taken with conventional systems and methods. Further, the higher flow rates of the liquid sample enables in capturing the rare cells in the liquid sample in much less time than the conventional systems and methods.

The methods and the systems of the present subject matter utilize a capture chip through which the liquid sample is flowed and a magnetic arrangement for magnetic capturing of the rare cells in the capture chip. The capture chip includes a longitudinal channel to facilitate the flowing of the liquid sample through the capture chip. The longitudinal channel has two parts, a first part and a second part, interfaced with each other. The second part has a narrower cross-sectional width than the first part. The capture chip also includes a capture well where the rare cells are magnetically captured. The capture well is near one end of the second part of the longitudinal channel, which is closer to an interfacing region between the first part and the second part. In an example, the capture well has a cross-sectional diameter of about 2 mm, which enables the capturing of the rare cells in a substantially small area.

The magnetic arrangement, according to the present subject matter, is in form of multiple rows of magnets. The magnetic arrangement has a first set of multiple rows of magnets that facilitates the magnetic capture of the rare cells in the first part of the longitudinal channel, during the flow of the liquid sample across the longitudinal channel. The first set of multiple rows includes a first row of magnets that spans the length of the first part of the longitudinal channel. Each subsequent row of first set of multiple rows of magnets has one magnet less than a previous row. The magnetic arrangement also has a second set of multiple rows of magnets that facilitates the magnetic capture of rare cells within the capture well. Each row of the second set of multiple rows of magnets at least has one capture magnet. The capture magnet is a magnet that has a cross-sectional area substantially equal to the coverage area of the capture well, so as to capture the rare cells within the capture well. The rows of the second set of multiple rows are appended to predefined last rows of the first set of multiple rows of magnets from an end away from the first row of the first set of multiple rows of magnets. In an example implementation, the rows of the second set may be appended to last two or three rows of the first set. The magnetic arrangement further has an isolated capture magnet having a cross-sectional area substantially equal to the coverage area of the capture well. The isolated capture magnet is a standalone magnet that does not belong to any row in the magnetic arrangement.

In order to magnetically capture the rare cells in the capture well, in accordance with the systems and methods of the present subject matter, the capture chip and the magnetic arrangement are moved with respect to each other to sequentially align the first part of the longitudinal channel with each of the multiple rows of the first set, one-by-one, and finally align the capture well with the isolated capture magnet. The magnets in each row of the magnetic arrangement are so placed that the magnetic poles of the magnets when aligned with the first part of longitudinal channel face the longitudinal channel. Also, the magnets in each row of the magnetic arrangement are so arranged that each pair of adjacent magnets in the respective row has opposite polarities facing the longitudinal channel of the capture chip. The opposite polarities of the adjacent magnet in each row enables in providing multi-well magnetic field along the longitudinal channel. The multi-well magnetic field may be understood as the magnetic field of high flux followed by low flux followed by high flux and so on. The number of magnetic field wells by a row may be one less than the number of magnets in the row.

In an implementation, the capture chip and the magnetic arrangement are moved with respect to each other to align the first part of the longitudinal channel with the first row of first set of multiple rows of magnets. As mentioned earlier, the first row of the first set spans the length of the first part of the longitudinal channel. As a result of alignment, the first part of the longitudinal channel comes under the influence of magnetic field of the magnets of the first row. The liquid sample is then flowed through the longitudinal channel from a capture chip inlet at the first part of the longitudinal channel to a capture chip outlet at the second part of the longitudinal channel. As the liquid sample flows through the longitudinal channel, the rare cell conjugated with magnetic particles get settled along the first part of the longitudinal channel due to the magnetic field of the magnets of the first row. After this, a wash liquid is flowed through the longitudinal channel from the capture chip inlet to the capture chip outlet. The wash buffer is flowed to wash away the non-specifically bound particles, i.e., the unbound particles, along the longitudinal channel. Non-specifically bound particles refer to the particles that are not conjugated with magnetic particles and may be settled along longitudinal channel.

After this, the capture chip and the magnetic arrangement are moved with respect to each other to align the first part of the longitudinal channel with subsequent rows of first set of multiple rows of magnets one by one, and, after each subsequent alignment, the wash liquid is flowed through the longitudinal channel from the capture chip inlet to the capture chip outlet. At a subsequent alignment, the first part of the longitudinal channel comes under the influence of magnetic field of the magnets of a subsequent row of the first set. Since the subsequent row has one less magnet than the previous row, at the subsequent alignment, the first part is under the influence of magnetic field of one less magnet with respect to that for the previous alignment. The magnetic arrangement is such that the first part is under the influence of magnetic field of one less magnet from the capture chip inlet side in each subsequent alignment. With each passing of the wash liquid, the rare cells settled in the first part are swept towards the capture well due to flowing of wash liquid and due to a gradient magnetic field being applied on the first part of the longitudinal channel through sequential alignment with the first set of multiple rows of magnets. Each passing of the wash liquid through the longitudinal channel is herein referred to as a wash liquid pass cycle.

Further, as mentioned earlier, the predefined last rows of the first set of multiple rows of magnets are appended with the second set of multiple rows. The magnetic arrangement is such that each of the predefined last rows of the first set is appended with at least one capture magnet. Also, the magnetic arrangement is such that when the first part of the longitudinal channel is aligned with each of the predefined last rows, the capture magnet of the second set gets aligned with the capture well. With such alignment and the passing of the wash buffer, the rare cells settled in the first part are swept into the capture well under the influence of magnetic field of the capture magnet.

After the alignment with all the rows of the first set of multiple rows of magnets and the passing of the wash buffer, the capture chip and the magnetic arrangement are moved with respect to each other to align the capture well with the isolated capture magnet of the magnetic arrangement. The wash liquid is flowed through the longitudinal channel once again. As a result, the rare cells are swept into the capture well.

The methods and the systems of the present subject matter facilitate efficient capturing of rare cells by sweeping the rare cells towards the capture well with each subsequent wash liquid pass cycle. The sweeping of the rare cells towards the capture well is enabled by providing a multi-well gradient magnetic field along the first part of the longitudinal channel up to the capture well. The multi-well gradient magnetic field is provided by sequentially aligning the first part of the longitudinal channel with each of the multiple rows of the first set and finally aligning the capture well with the isolated capture magnet. With this, a substantial number of rare cells can be efficiently captured in a substantially small area even if liquid sample is flowed at higher flow rates. Also, since the rare cells are captured in the capture well of substantially small area, the rare cells can be detected in substantially less time.

Although, the method and the systems of the present subject matter are described in context of application in the field of immunomagnetic capture and detection of rare cells; the methods and the systems of present subject matter can also be applied to any application that requires separation of magnetically conjugated molecules from a liquid sample. For example, the methods and the systems of the present subject matter can also be applied for removal of rare cells from a liquid sample for the purification of the liquid sample.

These and other advantages of the present subject matter would be described in greater detail in conjunction with the following figures. It should be noted that the description and figures merely illustrate the principles of the present subject matter.

FIG. 1 illustrates a cell capturing system 100 for magnetic capturing of rare cells from a liquid sample, in accordance with an implementation of the present subject matter. The cell capturing system 100 hereinafter may be referred to as the system 100. It may be noted that the rare cells in the liquid sample are conjugated at least with magnetic particles for the purpose of magnetic capture of the rare cells. In an example implementation, the rare cells may also be conjugated with fluorescent particles for the purpose of fluorescent detection of rare cells, after the magnetic capture. The preparation of liquid sample with conjugated rare cells is described later in the description.

The system 100 includes a storage and pumping system 102 for storing the liquid sample and a wash liquid, and passing the liquid sample and the wash liquid through a capture chip 104 of the system 100. The wash liquid may include bovine serum albumin (BSA), Dithiothreitols (DTT) and other salt to maintain osmotic balance. The storage and pumping system 102 has a liquid sample reservoir 106-1 which stores the liquid sample, and includes a wash liquid reservoir 106-2 which stores the wash liquid. The storage and pumping system 102 also has a valve 108 connected to the liquid sample reservoir 106-1 via a sample connecting tube 110 and to the wash liquid reservoir 106-2 via a wash liquid connecting tube 112, as shown. The valve 108 can be operated to selectively draw either the liquid sample from the liquid sample reservoir 106-1 or the wash liquid from the wash liquid reservoir 106-2 at an instance of time. The storage and pumping system 102 further has a pump 114. The pump 114 is connected to the valve 108 via a valve connecting tube 115, and connected to the capture chip 104 via a pump connecting tube 116. The pump 114 is operated to pump the liquid sample or the wash liquid through the capture chip 104, depending on the selection by the valve 108.

In an implementation, the pump 114 can be operated to pump the liquid sample through the capture chip 104 at different flow rates, for the purpose of capturing the rare cells in the liquid sample. In an example, the flow rate of the liquid sample can be in a range from about 200 µl/min to about 1000 µl/min.

The capture chip 104 has a longitudinal channel (not shown in FIG. 1) extending from a capture chip inlet 118 to a capture chip outlet 120. The pump connecting tube 116 connects the pump 114 with the longitudinal channel of capture chip 104 at the capture chip inlet 118. The pump 114 pumps the liquid sample or the wash liquid from the capture chip inlet 118 to the capture chip outlet 120 through the longitudinal channel of the capture chip 104.

The capture chip 104 further has a capture well (not shown in FIG. 1) where the rare cells are magnetically captured, in accordance with present subject matter. The capture well is in the form of a small pit of a cross-sectional diameter of about 2 mm. The details of longitudinal channel and the capture well of the capture chip 104 are described later with respect to description of FIG. 2.

The system 100 also has a magnetic arrangement 122 that includes a plurality of magnets arranged in multiple rows. The magnetic arrangement 122 and the capture chip 104 are moved with respect to each other to sequentially align different rows of magnets, one-by-one, with the longitudinal channel of the capture chip 104 for magnetic capturing of the rare cells in the capture well of the capture chip 104. As shown, the magnetic arrangement 122 is placed on a base plate 124. In an implementation, the base plate 124 may be moved to align a row of magnets with the longitudinal channel of the capture chip 104. The magnets in each row are so placed on the base plate 124 that, when magnets are aligned, the magnetic poles of the magnets face the capture chip 104. Further, the magnets in each row are so arranged that any pair of adjacent magnets in the respective row has opposite polarities facing the longitudinal channel of the capture chip 104.

As shown, the magnetic arrangement 122 has a first set 126 of multiple rows of magnets, a second set 128 of multiple rows of magnets, and an isolated capture magnet 130. The first set 126 of multiple rows includes a first row 132 of magnets that spans the length of a first part (not shown in FIG. 1) of the longitudinal channel. As described later in the description with reference to FIGS. 3(a) and 3(b) the longitudinal channel of the capture chip 104 has a first part and a second part, where the first part is wider than the second part. The wider first part carries a relatively larger volume of the liquid sample or the wash liquid than the second part. The narrower second part enables in restricting the flow of the liquid sample and the wash liquid over the capture well.

Further, each subsequent row of first set 126 of multiple rows has one magnet less than a previous row. Each subsequent row of the first set 126 has one less magnet from the side of the capture chip inlet 118. In the example implementation shown in FIG. 1, the first row 132 of the first set 126 has five magnets. Further, a second row 134 of the first set 126 has four magnets, i.e., one less magnet than the first row from the capture chip inlet 118. Similarly, a third row 136 of the first set 126 has three magnets, a fourth row 138 of the first set 126 has two magnets, and a fifth row 140 of the first set 126 has one magnet. In an example implementation, each row of magnets in the first set 126 is at a distance of about 1 cm or more from the adjacent row of magnets in the first set 126.

Further, in an implementation, the dimensions of each magnet in the first set 126 of multiple rows of magnets 126 may be such that the respective magnet spans the width of the first part of the longitudinal channel of the capture chip 104. For example, in case the magnet is a cylindrical magnet, the cross-sectional diameter of the magnet may be equal to the width of the first part of the longitudinal channel.

In the second set 128 of multiple rows of magnets each row has one capture magnet having a cross-sectional area substantially equal to a coverage area of the capture well. In the implementation shown in FIG. 1, the second set 128 has two rows, each row having a capture magnet referenced by 142 and 144, respectively. Further, as shown, the two rows of the second set 128 are appended to the last two rows of the first set 126. Thus, when the first part of the longitudinal channel is aligned with any of the last two rows of the first set 126, the capture magnet of the appended row of the second set 128 aligns with the capture well of the capture chip 104. The purpose of the capture magnet of the rows of the second set 128 is to magnetically capture the rare cells within the capture well.

Further, the isolated capture magnet 130 of the magnetic arrangement 122 is a standalone magnet that does not belong to any row. The isolated capture magnet 130 also has a cross-sectional area substantially equal to the coverage area of the capture well. The purpose of the isolated capture magnet 130 is to ensure that the rare cells which are captured in the longitudinal channel due to the different rows of magnetic arrangement 122 are finally captured within the capture well. The procedure of magnetic capturing of the rare cells, from the liquid sample, using the capture chip 104 and the magnetic arrangement 122 are described later in the description.

Figure 2:
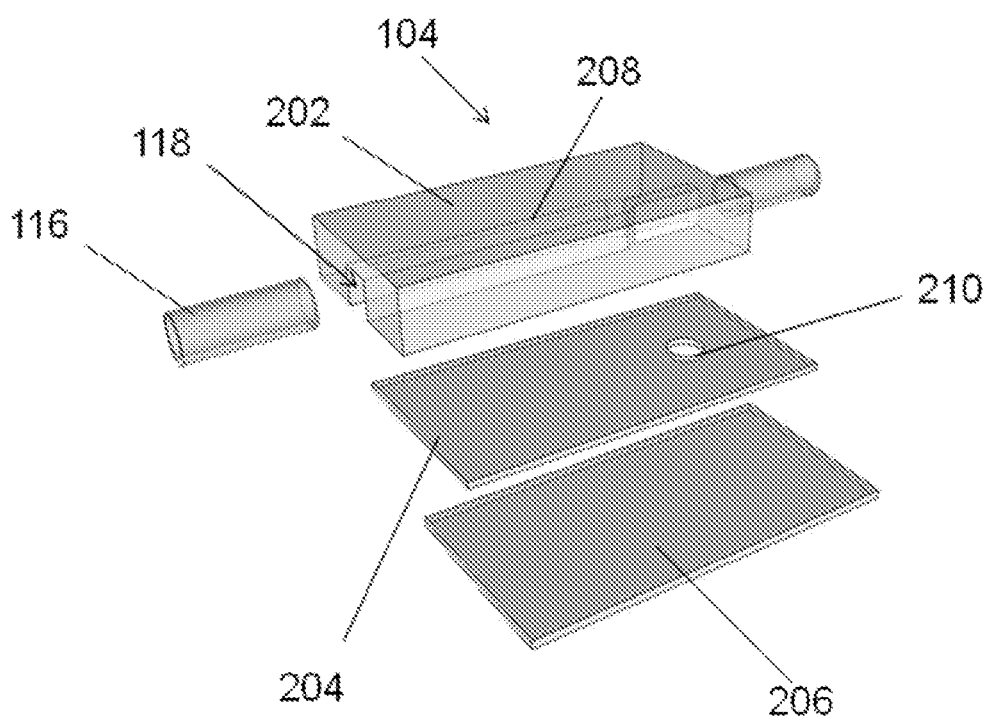
FIG. 2 illustrates a capture chip of the cell capturing system, in accordance with an implementation of present subject matter.

FIG. 2 illustrates the capture chip 104 of the cell capturing system 100, in accordance with an implementation of present subject matter. As shown, the capture chip 104 is realized by three layers, namely a first layer 202, a second layer 204, and a third layer 206, one on top of the other. The second layer 204 is sandwiched between the first layer 202 and the third layer 206. In an example implementation, the first layer 202 is made of a polydimethyl siloxane (PDMS), PMMS, polystyrene, acrylonitrile butadiene styrene, or polypropylene. The first layer 202 has the longitudinal channel 208 which runs along the length of the first layer 202, as shown. The longitudinal channel 208 is a groove at the bottom surface of the first layer 202. One end of the longitudinal channel 208 forms the capture chip inlet 118 and the other end of the longitudinal channel 208 forms the capture chip outlet 120. As mentioned earlier, the pump connecting tube 116 is connected at the capture chip inlet 118, so that the pump 114 can pump the liquid sample or the wash liquid through the longitudinal channel 208. The details of the longitudinal channel 208 are described in details later with reference to FIGS. 3(*a*) and 3(*b*).

The second layer 204 is coupled to the first layer 202, such that the second layer 204 covers the opening along the longitudinal channel 208 of the first layer 202. The portion of the second layer 204 that covers the opening along the longitudinal channel 208 forms the base of the longitudinal channel 208. The base of the longitudinal channel 208 may thus be understood as a surface, formed by the second layer 204, on which the rare cells are magnetically captured on passing of the liquid sample through the longitudinal channel 208. In an implementation, the second layer 204 of the capture chip 104 may be a polymeric sheet made of parafilm M®, or polypropylene. The polymeric sheet avoids the non-specific binding of rare cells and other particles from the liquid sample along the longitudinal channel 208. In an implementation, the second layer 204 may have a thickness of about 100 μm to 200 μm.

The second layer 204 has a through hole 210, as shown. The position of the through hole 210 in the second layer 204 is such that, in the assembled state of the layers of the capture chip 104, the through hole 210 aligns, and is in-line, with the longitudinal channel 208 of the first layer 202. The position of the through hole 210 with respect to the longitudinal channel 208 is shown in FIGS. 3(*a*) and 3(*b*). In an example implementation, the through hole 210 has a cross-sectional diameter of about 2 mm.

The third layer 206 of the capture chip 104 may be a glass cover slide of a thickness of about 170 μm. The third layer 206 is coupled to the second layer 204, such that the third layer 206 covers the through hole 210 in the second layer 204 from one end to form the capture well. The portion of the third layer 206 covering the through hole 210 forms the base of the capture well. The capture well has a depth equal to the thickness of the second layer 204. The other end of the through hole 210 opens towards the longitudinal channel in order to collect the rare cells in the capture well. With the third layer 206 being a glass cover slide, the rare cells captured within the capture well can be viewed through the third layer using an imaging device.

FIG. 3(*a*) illustrates a sectional view of the first layer 202 of the capture chip 104 to show the longitudinal channel 208 and the capture well 302 of the capture chip 104, in accordance with an implementation of the present subject matter. As mentioned earlier, the capture well 302 is formed by the through hole 210 in the second layer 204 and the base formed by the third layer 206. The longitudinal channel 208 runs from the capture chip inlet 118 to the capture chip outlet 120 along the length of the capture chip 104. The longitudinal channel 208 is divided into two parts, the first part 304 and the second part 306, interfaced to each other. The first part 304 of the longitudinal channel 208 has a width of about 4 mm, according to an implementation of the capture chip 104.

The second part 306 of the longitudinal channel 208 has a narrower width as compared to that of the first part 304 of the longitudinal channel 208. It is to be noted that the first part 304 can have a width larger than 4 mm. The wider first part 304 can accommodate larger volumes of the liquid sample passing through the longitudinal channel 208. The width of the second part 306 of the longitudinal channel 300 is substantially equal to the cross-sectional diameter of the capture well 302, i.e., the cross-sectional diameter of the through hole 210. This enables in restricting the flow of the liquid sample over the capture well 302. Such a restricted flow of the liquid sample facilitates increasing the possibility of the rare cells, passing over the capture well, to get captured in the capture well 302.

Further, as shown in FIG. 3(*a*), the first part 304 and the second part 306 of the longitudinal channel 300 are interfaced with each other through an interfacing region 308. The interfacing region 308 of the longitudinal channel 208 is shaped such that the transition from the wider first part 304 to the narrower second part 306 is substantially smooth. With this, the flow of the liquid sample or the wash liquid from the wider first part 304 to the narrower second part 306 is substantially uniform.

Figure 3A:
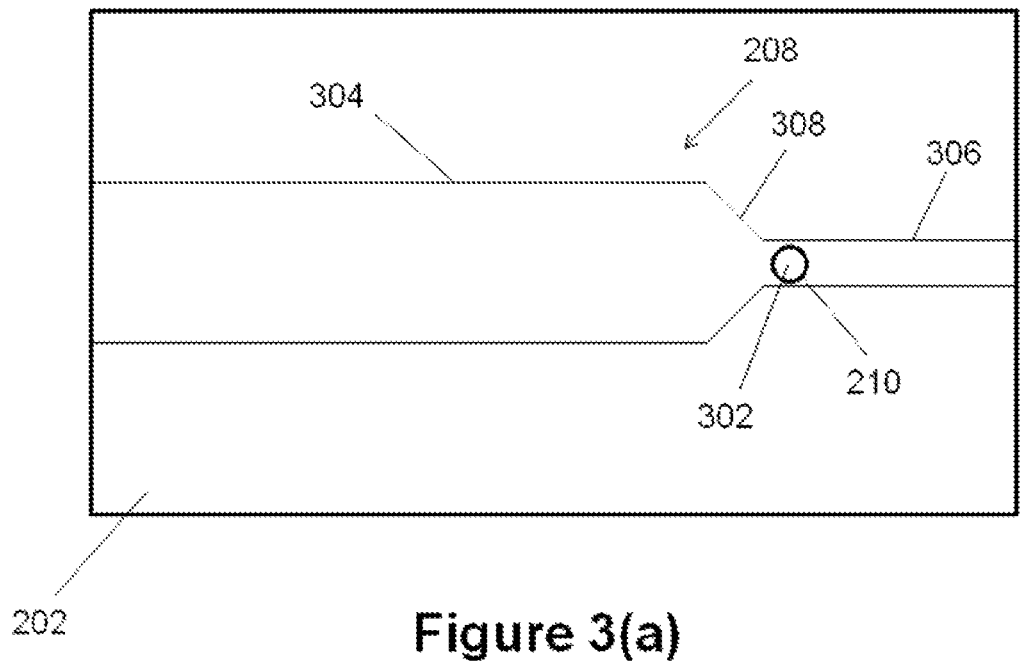
FIG. 3(a) illustrates a sectional view of the first layer of the capture chip to show the longitudinal channel and the capture well of the capture chip, in accordance with an implementation of the present subject matter.
Figure 3B:
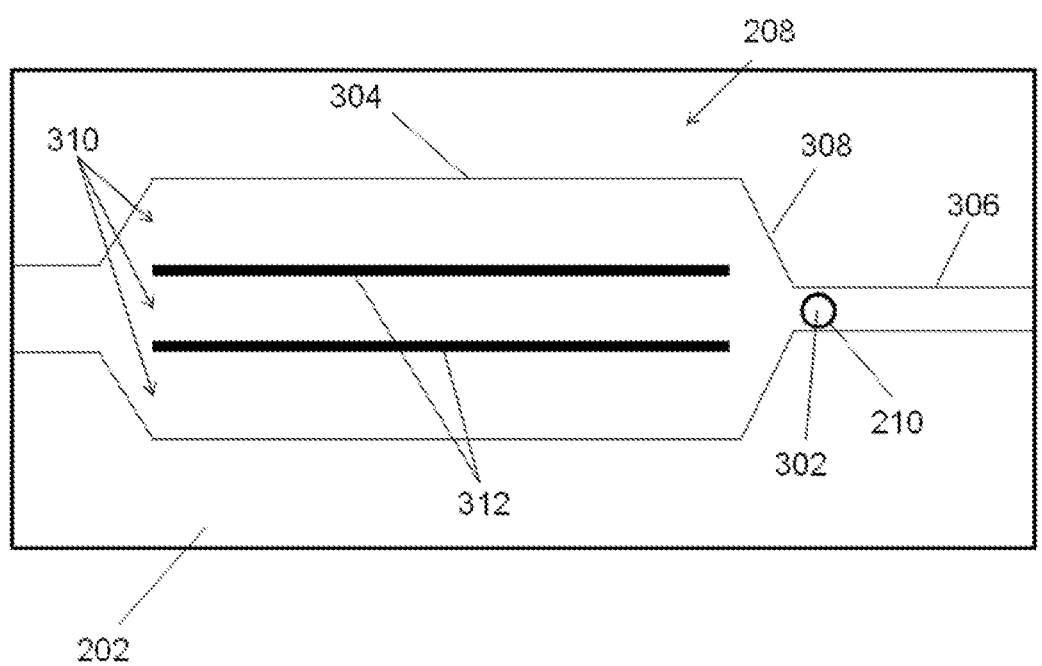
FIG. 3(b) illustrates a sectional view of the first layer of the capture chip to show the longitudinal channel and the capture well of the capture chip, in accordance with another implementation of the present subject matter.

FIG. 3(b) illustrates a sectional view of the first layer 202 of the capture chip 104 to show the longitudinal channel 208 and the capture well 302 of the capture chip 104, in accordance with another implementation of the present subject matter. The longitudinal channel 208 is the first part 304 wider than the second part 306. In this implementation, the second part 306 of the longitudinal channel 208 and the capture well 302 are similar to the ones shown in FIG. 3(a). The first part 304 of the longitudinal channel 208 has a width of about 16 mm. As shown, the first part 304 is divided into three different sub-channels 310 along its width. The sub-channels 310 are formed by introducing two PDMS blocks 312 along the first part 304, as shown. The width of each of the PDMS blocks 312 is about 2 mm. Each PDMS block 312 is placed such that each sub-channel 310 has a width of about 4 mm.

Further, as shown in FIG. 3(b), the first part 304 and the second part 306 of the longitudinal channel 300 are interfaced with each other through an interfacing region 308. As in the case of the implementation shown in FIG. 3(a), the interfacing region 308 of the longitudinal channel 208 is also shaped to provide a substantially smooth transition from the wider first part 304 to the narrower second part 306.

Although the implementation of FIG. 3(b) depicts three sub-channels 310 in the first part 304, the number of sub-channels can be two or more. The number of sub-channels may depend on the width of the first part 304. The number of sub-channels may be such that the width of the first part is divided into sub-channels of substantially equal widths. With a wider first part 304, a higher volume of liquid sample can be passed through the longitudinal channel 208 of the capture chip 104. The division of the wider first part 304 into multiple sub-channels facilitates a uniform flow of liquid sample or wash liquid through the first part 304 of longitudinal channel 208.

Figure 4A:
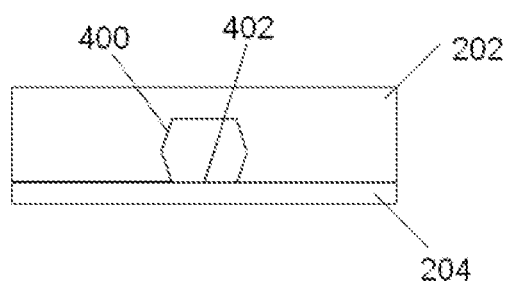
FIGS. 4(a), 4(b), and 4(c) illustrate different possible cross-sections of the first part of the longitudinal channel, in accordance with implementations of the present subject matter.
Figure 4B:
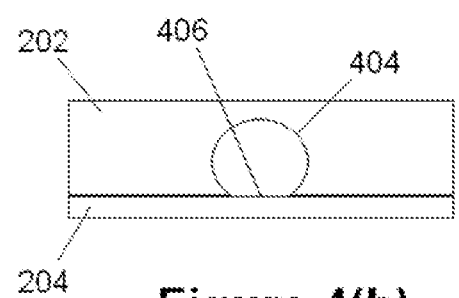
Figure 4C:
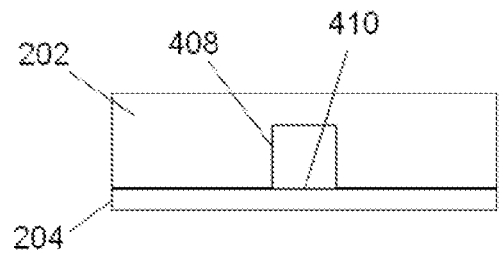

FIGS. 4(a), 4(b), and 4(c) illustrate different possible cross-sections of the first part 304 of the longitudinal channel 208, in accordance with implementations of the present subject matter. FIG. 4(a) illustrates a hexagonal cross-section 400 of the longitudinal channel 208 in the first layer 202. The base of the longitudinal channel 208, which is formed by a portion of the second layer 204 covering the opening along the longitudinal channel 208, is referenced by 402. The base 402 of the longitudinal channel 208 has a width equal to one side of the hexagonal cross-section 400. In an example implementation, each side of the hexagonal cross-section 400 is about 4 mm. Thus, the base 402 of the longitudinal channel 208 has a width of about 4 mm.

FIG. 4(b) illustrates a circular cross-section 404 of the longitudinal channel 208. As shown, the circular cross-section 404 is formed by a partial circle. In an example implementation, the partial circle may be a semi-circle or more than a semi-circle but less than a full circle. In an implementation, the dimension of the circular cross-section 404 is such that the base of the longitudinal channel 208, referenced by 406, has a width of about 4 mm.

FIG. 4(c) illustrates a square cross-section 408 of the longitudinal channel 208. The base of the longitudinal channel 208, referenced by 410, has a width equal to one side of the square cross-section 408. In an example implementation, each side of the square cross-section 408 is about 4 mm. Thus, the base 410 of the longitudinal channel 208 has a width of about 4 mm.

It may be understood that the different cross-sections of the longitudinal channel 208 illustrated in FIGS. 4(a), 4(b), and 4(c) are example illustrations, and other cross-sections are also possible. While describing FIGS. 3(a) and 3(b), the width of the longitudinal channel 208 is mentioned. It may be noted that the width of the longitudinal channel 208 is equivalent to the width of the base of the longitudinal channel 208.

Figure 5A:
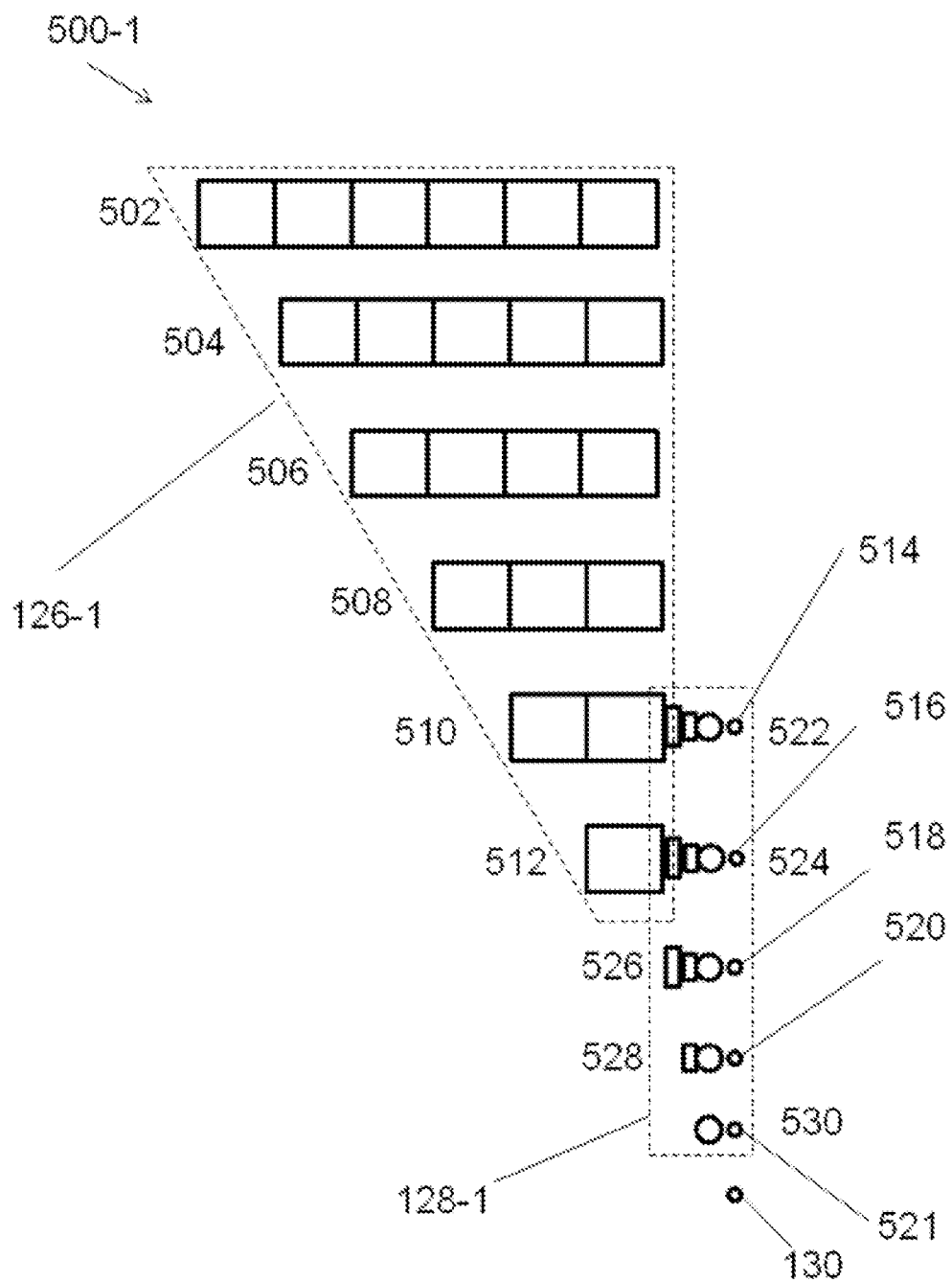
FIG. 5(a) illustrates a magnetic arrangement of the cell capturing system, in accordance with an implementation of the present subject matter.

FIG. 5(a) illustrates a magnetic arrangement 500-1 of the cell capturing system 100, in accordance with an implementation of the present subject matter. The magnetic arrangement 500-1 of said implementation may be used for the case where the capture chip 104 has the longitudinal channel 208 as shown in FIG. 3(a). The magnetic arrangement 500-1 has a first set 126-1 of multiple rows of magnets and a second set 128-1 of multiple rows of magnets. Besides these, the magnetic arrangement 500-1 also has an isolated capture magnet 130 which is a standalone magnet, and not a part of any magnet row.

As shown in FIG. 5(a), the first set 126-1 has six rows of magnets, with magnets in each row having a width at least equal to the width of the longitudinal channel 208. The first row 502 of the first set 126-1 of multiple rows has six magnets that span the length of the first part 304 of the longitudinal channel 208. The second row 504 of the first set 126-1 of multiple rows has five magnets, i.e., one magnet less than the first row 502. The first set 126-1 of multiple rows further has a third row 506 with four magnets, a fourth row 508 with three magnets, a fifth row 510 with two magnets, and a sixth row 512 with one magnet. With each subsequent row of the first set 126-1 having one magnet less than the previous row in the first set 126-1 of multiple rows, a gradient magnetic field is established along the first part 304 of the longitudinal channel 208, when the longitudinal channel 208 is sequentially aligned with the rows of the first set 126-1 of multiple rows of magnets, during the magnetic capturing of rare cells. The gradient magnetic field with the sequential alignment and the passing of the wash liquid enable sweeping of the rare cells towards the capture well 302.

Although, the magnetic arrangement 500-1 shown in FIG. 5(a) has six rows of magnets in the first set 126-1 and six magnets in the first row 502 of the first set 126-1; however, in an implementation, the magnetic arrangement may have more or less than six rows of magnets in the first set and more or less than six magnets in the first row of the first set.

It may be noted that the number of magnets in the first row of the first set may depend on the flow rate of the liquid sample through the system 100. The number of rows of magnets in the first set may depend on the number of magnet in first row.

Further, as shown in FIG. 5(a), in the second set 128-1 of multiple rows of magnets, each row has one capture magnet 514, 516, 518, 520, 521. The capture magnet 514, 516, 518, 520, 521 in each row of the second set 128-1 has a cross-sectional area substantially equal to the coverage area of the capture well 302. As shown, each row of the second set 128-1 also has a number of interfacing magnets. The first row 522, the second row 524, and the third row 526 of the second set 128-1 has three interfacing magnets that span the length of the interfacing region 308 in the longitudinal channel 208. The width of the three magnets in the first row 522, in the second row 524, and in the third row 526 of the second set 128-1 varies according to the variation in the width of the interfacing region 308 between the first part 304 and the second part 306 of the longitudinal channel 208.

The number of interfacing magnets and the number of rows with the interfacing magnets in the second set 128-1 depend on the length of the interfacing region 308. Further, as shown, the first two rows 522 and 524 of the second set 128-1 are appended to the last two rows, i.e., the fifth row 510 and the sixth row 512, of the first set 126-1. It may be noted that the third row 526 of the second set 128-1 is an independent row, i.e., not appended to any row of the first set 126-1. Each row subsequent to the third row 526 of the second set 128-1 has one less interfacing magnet than the previous row of the second set 128-1. The fourth row 528 of the second set 128-1 has two interfacing magnets, and the fifth row 530 of the second set 128-1 has one interfacing magnet. With each row subsequent to the third row 526 in the second set 128-1 having one less interfacing magnet than the previous row, a gradient magnetic field is established along the interfacing region 308 of the longitudinal channel 208, when the longitudinal channel 208 gets sequentially aligned with the fourth row 528 and the fifth row 530 of the second set 128-1, during the magnetic capturing of rare cells. This gradient magnetic field with the sequential alignment and the flow of the wash liquid enable sweeping of the rare cells towards the capture well 302.

It may be noted that when the first part 304 of the longitudinal channel 208 of the capture chip 104 is made to align with a row of the first set 126-1 to which a row of second set 128-1 is appended, the capture well 302 gets aligned with the capture magnet of the row of the second set 128-1. Also, the interfacing region 308 of the longitudinal channel 208 gets aligned with the interfacing magnets of the row of the second set 128-1. This ensures that the capture well 302 and the interfacing region 308 lie under the influence of magnetic field and the rare cells that may flow through the longitudinal channel 208 are captured within the capture well 302.

Figure 5B:
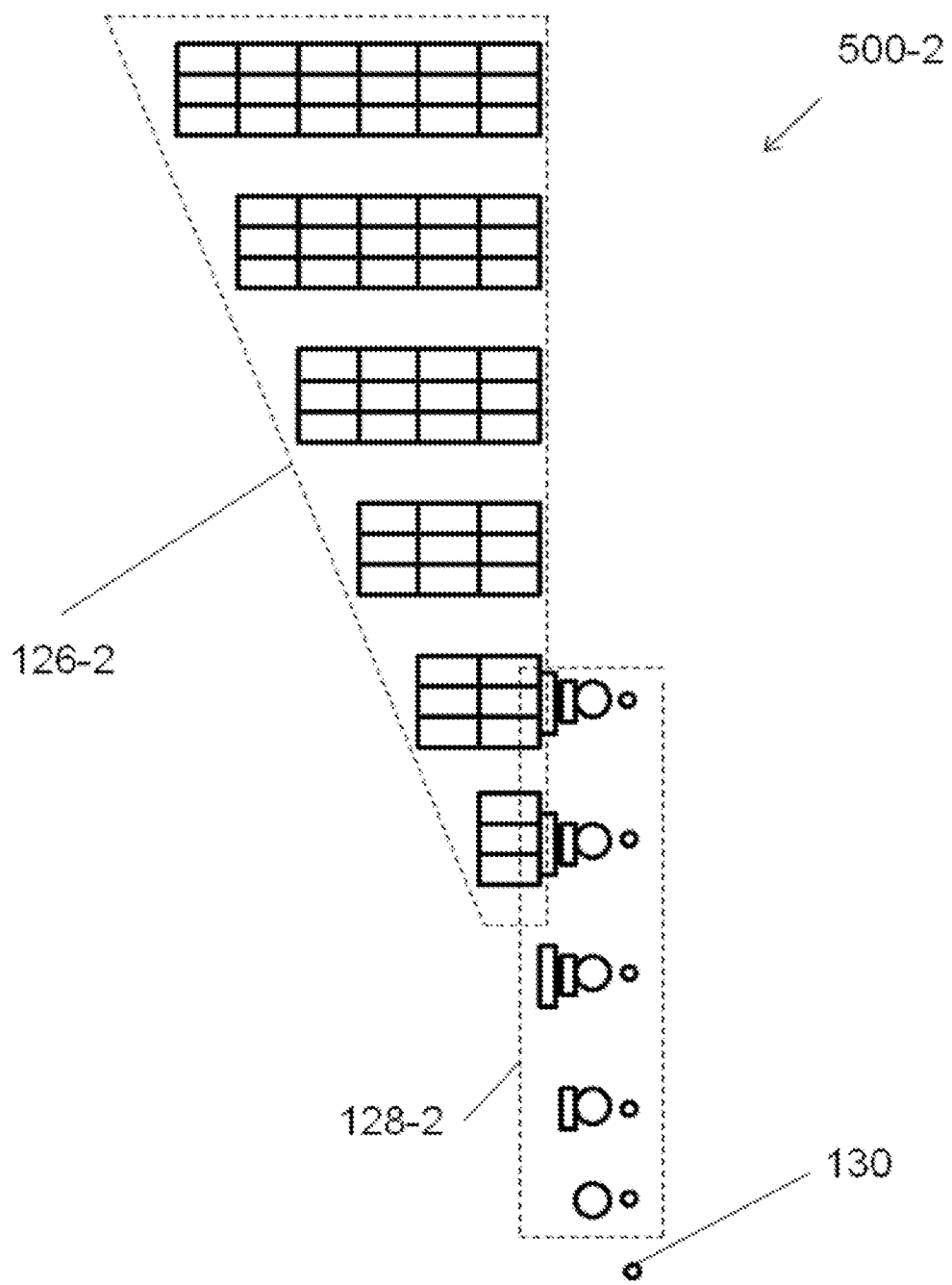
FIG. 5(b) illustrates a magnetic arrangement of the cell capturing system, in accordance with an implementation of the present subject matter.

FIG. 5(b) illustrates a magnetic arrangement 500-2 of the cell capturing system 100, in accordance with an implementation of the present subject matter. The magnetic arrangement 500-2 of said implementation may be used for the case where the capture chip 104 has the longitudinal channel 208 as described in FIG. 3(b). As mentioned earlier, the longitudinal channel 208 of FIG. 3(b) is divided into three sub-channels 310 with the help of two PDMS blocks 312. Each of the sub-channels 310 may be of a width of about 4 mm, and each of the PDMS block 312 may be of a width of about 2 mm. The magnetic arrangement 500-2 has a first set 126-2 of multiple rows of magnets, a second set 128-2 of multiple rows of magnets, and an isolated capture magnet 130 which is a standalone magnet, and not a part of any magnet row.

It may be appreciated that magnetic arrangement 500-2 of FIG. 5(b) is similar to the magnetic arrangement 500-1 of FIG. 5(a), with the first set 126-2 having six rows of magnets, and the second set 128-2 has five rows of magnets. Each row of the second set 128-2 has a capture magnet and a number of interfacing magnets similar to the ones shown in FIG. 5(a).

As shown in FIG. 5(b), each row of the first set 126-2 is divided into three sub-rows of magnets. The number of sub-rows in each row of the first set 126-2 is equal to the number of sub-channels 310 in the longitudinal channel 208, such that one sub-row of magnets aligns with one sub-channel in the longitudinal channel 208. The magnets in each sub-row have a width at least equal to the width of the sub-channel to which the sub-row gets aligned.

The description below describes the preparation of the liquid sample with rare cells conjugated with magnetic and fluorescent particles. Initially, the magnetic and fluorescent particles may be conjugated with a binding agent, for example, antibodies, peptides, or aptamers, which can bind with the rare cells to be captured. After conjugation of the magnetic and fluorescent particles with the binding agent, the conjugated magnetic and fluorescent particles are incubated with the liquid sample having the unconjugated rare cells. As a result of incubation, the rare cells get conjugated with the magnetic and fluorescent particles through the binding agent.

In an example, the rare cells that can be conjugated for capturing may include, Eukarya, Prokarya, Archaea, Viruses, proteins, and such. In an example, the liquid sample with the rare cells can be of a viscosity of about 10 centipoise or less. In case the liquid sample is of a higher viscosity, the liquid sample can be diluted with a wash buffer, before using in the system 100.

In an example, the magnetic particles can be of a diameter in a range from about 20 nm to about 5000 nm. The magnetic particles can be paramagnetic particles, supermagnetic particles, or ferromagnetic particles.

In an example, the fluorescent particles may include dyes like fluorescein isothiocynate, Texes Red, Cy5, Cy7, tetramethylrhodamine isothiocyanate, and 4,6-diamidino-2-phenylinode. The fluorescent particles can be used as single molecules or a cluster of molecules.

The description hereinafter describes the operation of the system 100 for magnetic capturing of rare cells in the capture well 302 of the capture chip 104 using the magnetic arrangement 122. As mentioned earlier, the magnet arrangement 122 is placed on the base plate 124. In one implementation, the base plate 124 may be coupled with a linear positioner which can be operated to move the base plate 124 and thus the magnetic arrangement 122 with respect to the capture chip 104 for the purpose of alignment of the longitudinal channel 208 with different rows of the magnetic arrangement 122. In an example, the alignment may be such that the distance between the capture chip 104 and the aligned row of magnets of the magnetic arrangement 122 may be equal to 1 mm or less.

Initially, the linear positioner is operated to move the magnetic arrangement 122 with respect to the capture chip 104, such that the first part 304 of the longitudinal channel 208 is aligned with the first row 132 of the first set 126 of multiple rows of magnets. As one may recall, the first row 132 spans the length of the first part 304 of the longitudinal channel 208. Thus, as a result of the alignment, the first part 304 of the longitudinal channel 208 comes under the influence of magnetic field of the magnets of the first row 304.

After aligning with the first row 132, the liquid sample containing the rare cells conjugated with the magnetic and fluorescent particles is flowed through the longitudinal channel 208 of the capture chip 104. For this, the valve 108 is operated to draw the liquid sample from the liquid sample reservoir 106-1, and the pump 114 is operated to flow the liquid sample from the capture chip inlet 118 to the capture chip outlet 120 through the longitudinal channel 208. Now due to the presence of magnetic field throughout the first part 304 and the presence of magnetic particles on the conjugated rare cells, the conjugated rare cells are magnetically settled on the base of the longitudinal channel 208 along the first part 304.

After this, the wash liquid is flowed through the longitudinal channel 208 of the capture chip 104. For this, the valve 108 is operated to draw wash liquid from the wash liquid reservoir 106-2, and the pump 114 is operated to flow the wash liquid from the capture chip inlet 118 to the capture chip outlet 120 through the longitudinal channel 208. The wash buffer is flowed to wash away the non-specifically bound particles, i.e., the unbound particles, along the longitudinal channel 208.

After this, the linear positioner is operated to move the magnetic arrangement 122 to align the first part 304 of the longitudinal channel 208 with the second row 134 of the first set 126. As one may recall, the second row 134 has one less magnet from the end nearer to the capture chip inlet 118. This implies that a region of the first part 304 of the longitudinal channel 208 that is close to the capture chip inlet 118, is no longer under the influence of a magnetic field and the conjugated rare cells which had earlier settled at that region are now free to move. Such conjugated rare cells may be referred to as free conjugated rare cells.

Now, the wash liquid is again flowed through the longitudinal channel 208 of the capture chip 104. For this, the valve 108 is operated to draw wash liquid from the wash liquid reservoir 106-2, and the pump 114 is operated to flow the wash liquid from the capture chip inlet 118 to the capture chip outlet 120 through the longitudinal channel 208. This passing of the wash liquid sweeps the free conjugated rare cells in the direction towards the capture well 302, under the influence of magnetic field of magnets in the second row 134. The free conjugated rare cells merge with the conjugated rare cells settled in the regions that are under the influence of magnets of the second row 134. With this, the number and the concentration of conjugated rare cells in the regions under the influence of magnets of the second row 134 increases.

After this, the linear positioner is operated to move the magnetic arrangement 122 to align the first part 304 of the longitudinal channel 208 with the third row 136 of the first set 126. Since the third row 136 has one less magnet than the second row 134, an additional region of the first part 304 of the longitudinal channel 300 is now not under the influence of any magnetic field, and more conjugated rare cells are free to move. At this, the wash liquid is again passed through the longitudinal channel 208. The free conjugated rare cells are swept in the direction towards the capture well 302 under the influence of magnetic field of magnets in the third row 136, and eventually merged with the conjugated rare cells in other regions that are under the influence of magnetic field of magnets of the third row 136.

After this, the linear positioner is operated to move the magnetic arrangement 122 to align the first part 304 of the longitudinal channel 300 with each of the subsequent rows of the first set 126, one-by-one, and the wash liquid is passed through the longitudinal channel 208 in order to sweep the conjugated rare cells towards the capture well 302.

It may be noted that when the first part 304 of the longitudinal channel 208 is aligned with a row of first set 126 to which a row of second set 128 is appended, the capture well 304 aligns with the capture magnet of the row of the second set 128. Further, in the implementation as described earlier where the longitudinal channel has an interfacing region and the rows of the second set has interfacing magnets along with the capture magnet, the interfacing region of the longitudinal channel aligns with the interfacing magnets of the same row of second set.

In the implementation as described earlier, the second set of multiple rows of magnets may include addition rows with interfacing magnets which are not appended to the rows of the first set. In said implementation, after the alignment with all the rows of the first set, the linear positioner is operated to move the magnetic arrangement to align the interfacing region of the longitudinal channel with each of the addition rows of the second set, and the wash liquid is passed through the longitudinal channel after each alignment. With this passing of wash liquid, the conjugated rare cells which are free to move in the interfacing region of the longitudinal channel sweep further towards the capture well. The steps of alignment and passing of the wash liquid are repeated until interfacing region of the longitudinal channel is aligned with all the rows of the second set of the multiple rows of magnets.

After alignments with the rows of the first set 126 and the second set 128, the linear positioner is operated to move the magnetic arrangement 122 to align the isolated capture magnet 130 with the capture well 302. After this alignment, the wash liquid is passed through the longitudinal channel 208. At this stage, since no region in the first part 304 and in the interfacing region 308 of the longitudinal channel 208 is under the influence of magnetic field, and only the capture well 302 is under the influence of magnetic field of the isolated capture magnet, the passing of the wash liquid sweeps the conjugated rare cells into the capture well 302. With this, the conjugated rare cells are magnetically captured within the capture well 302. It may be understood that all the conjugated rare cells, which are settled along the first part 304 of longitudinal channel 208 after the passing of the liquid sample, may get captured within the capture well 302.

Figure 6:
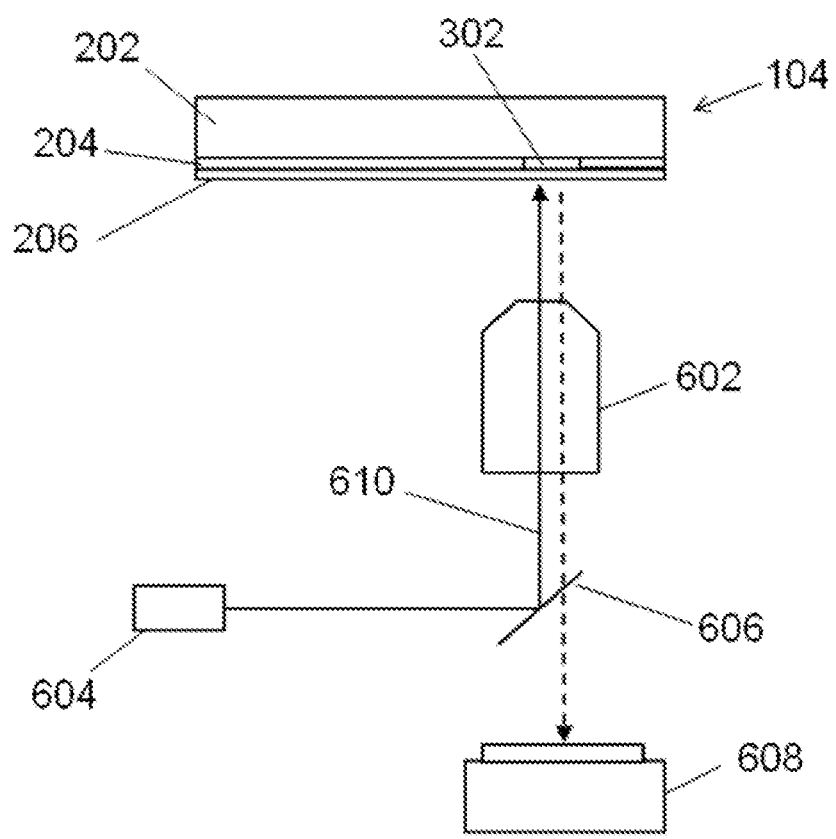
FIG. 6 illustrates an imaging apparatus for detection of the magnetically captured rare cells, in accordance with an implementation of the present subject matter.

FIG. 6 illustrates an imaging apparatus 600 for detection of the magnetically captured rare cells, in accordance with an implementation of the present subject matter. The imaging apparatus 600 implements a fluorescent-based imaging to detect the rare cells conjugated with the magnetic and fluorescent particles, and captured in the capture well 302. As shown, the imaging apparatus 600 includes an objective lens 602, a light source 604, a beam splitter 606, and a sensor 608. The objective lens 602 is a long working distance lens with 40× or 60× magnification. The objective lens 602 is positioned such that the light from the objective lens 602 can pass through the third layer 206 to the capture well 302 to excite the fluorescent particle conjugated on the rare cells. The light source 604 may include a laser diode or a light emitting diode of a wavelength of about 488 nm or 532 nm. The beam splitter 606 may be a dichroic mirror capable of reflecting the light beam from the light source and also separate the light beam due to the fluorescent emission from the conjugated rare cells and the light beam reflected by the capture chip 104. The sensor 708 may include a charge couple device (CCD) sensor or a complimentary metal oxide semiconductor (CMOS) sensor that can detect the light emitted by the fluorescent particles upon their excitation.

In order to detect the rare cells, a light beam 610 from the light source 604 is made incident on the beam splitter 606. The beam splitter 606 reflects the light beam 610. The light beam 610 is focused on the back focal plane of the objective lens 602, and made incident to the third layer 206 of the capture chip 104 through the objective lens 602. As the light beam 610 is made incident on the third layer 206 of the capture chip 104, a portion of the light beam 610 is reflected by the third layer 206, and a portion of the light beam 610 is passed to the rare cells in the capture well 302. The portion that passes to the rare cells in the capture well 104 excites the fluorescent particles conjugated with the rare cells. As a result, a fluorescent light beam is emitted from the fluorescent particles on rare cells.

Further, the reflected light beam from the third layer 206 and the fluorescent light beam from the fluorescent particles are captured by the objective lens 602 passed to the beam splitter 606. The beam splitter 606 separates the reflected light beam and the fluorescent light beam and the fluorescent light beam is passed onto the sensor 608. The fluorescent light beam is detected by the sensor 608, and the signal from the sensor 608 is processed to obtain a fluorescent image. The fluorescent image is the image of region of the capture well 302 from where the fluorescent light is emitted, captured by the objective lens, and detected by the sensor 608. The above described imaging process may be repeated in order to obtain images of different regions of the capture well 302.

Figure 7A:
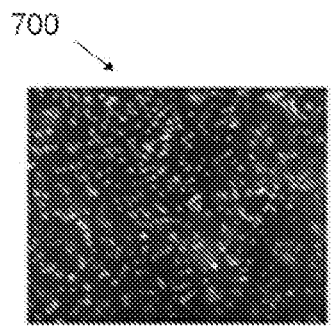
FIGS. 7(a), 7(b), 7(c), 7(d), and 7(e) illustrate fluorescent images depicting the captured rare cells imaged with the imaging apparatus, in accordance with an implementation of the present subject matter.
Figure 7B:
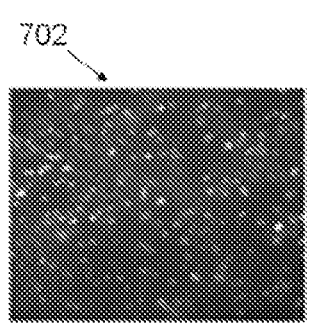
Figure 7C:
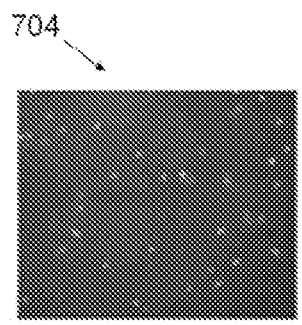
Figure 7D:
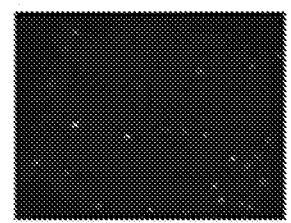
Figure 7E:
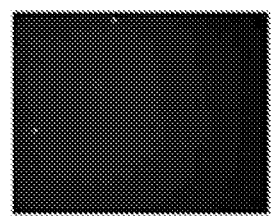

FIGS. 7(a), 7(b), 7(c), 7(d), and 7(e) illustrate fluorescent images depicting the captured rare cells imaged with the imaging apparatus 600, in accordance with an implementation of the present subject matter. For examples shown herein, the flow rate of the liquid sample is 500 µl/min and 1 ml of liquid sample is passed through the system 100 where the number of magnets in the first row of the first set of rows is 8. FIG. 7(a) illustrates a fluorescent image 700 of the captured rare cells, when the liquid sample has a concentration of about $10^6$ CFU/ml. FIG. 7(b) illustrates a fluorescent image 702 of the captured rare cells, when the liquid sample has a concentration of about $10^5$ CFU/ml. FIG. 7(c) illustrates a fluorescent image 704 of the captured rare cells, when the liquid sample has a concentration of about $10^4$ CFU/ml. FIG. 7(d) illustrates a fluorescent image 706 of the captured rare cells, when the liquid sample has a concentration of about $10^3$ CFU/ml. FIG. 7(e) illustrates a fluorescent image 708 of the captured rare cells, when the liquid sample has a concentration of about $10^2$ CFU/ml.

In the fluorescent images 700, 702, 704, 706, and 708 the illuminated spots depict the fluorescent particles conjugated with the rare cells in the capture well 302. The count of illuminated spots can be approximated to estimate the number of fluorescent markers, and thus estimate the number of conjugated rare cells captured in the capture well 302. It may be appreciated from the fluorescent images 704, 706, and 708 that even at lesser concentrations of the liquid sample, for instance, $10^4$ or $10^3$ or $10^2$ CFU/ml, the system 100 is able to magnetically capture a substantially large number of conjugated rare cells within the small coverage area of the capture well 302. Also, the conjugated rare cells can be magnetically captured at a high flow rate of about 500 µl/min, since the number of magnets in the first row of magnets in the first set is 8 and the number of rows of magnets in the first set is 8. FIGS. 7(a), 7(b), 7(c), 7(d), and 7(e) show the illuminated spots, depicting the conjugated rare cells, when 1 ml of liquid sample at various concentrations from $10^2$ to $10^6$ CFU/ml is passed through the system 100. In an implementation, illuminated spots depicted the conjugated rare cells can be imaged when 10 ml of liquid sample at a concentration of about 1 CFU/ml is passed through the system 100.

In an example implementation, the cell capturing system 100 can be used for purification of high volumes of liquid sample by capturing and removal of rare cells from the liquid sample. For this, a plurality of capture chips 104 can be stacked together in the system 100 to simultaneously process higher volume of liquid sample to capture rare cells from the liquid sample and obtain higher volume of purified liquid sample at the capture chip outlet. In an example, 10 capture chips 104 may be stacked in order to capture rare cells from a liquid sample and obtain 10 times more volume of purified liquid sample in the same duration. In an example, the liquid sample can be a blood sample and the rare cells can be disease rare cells, such as, circulating tumor cells. In an example implementation, the system 100 can be used to cure a disease. For this, the blood may be drawn. The drawn blood may be passed through the system 100 to capture the disease rare cells and obtain the purified blood. The purified blood can then be transfused.

Figure 8:
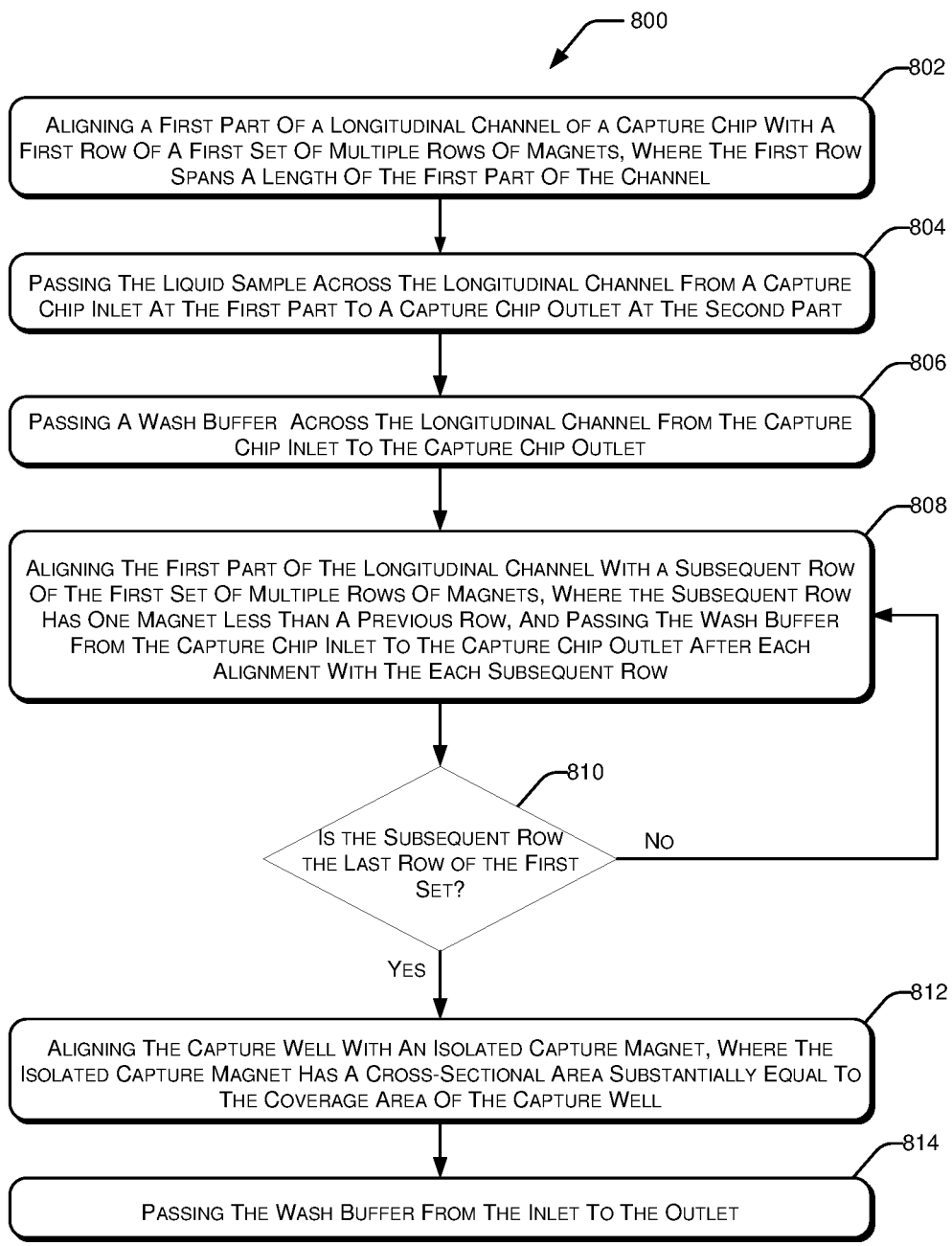
FIG. 8 illustrates a method of magnetic capturing of rare cells from a liquid sample, in accordance with an implementation of the present subject matter.

FIG. 8 illustrates a method 800 of magnetic capturing of rare cells from a liquid sample, in accordance with an implementation of the present subject matter. The order in which the method 800 is described is not intended to be construed as a limitation, and any number of the described method blocks can be combined in any order to implement the method 800, or any alternative methods. Additionally, individual blocks may be deleted from the method 800 without departing from the scope of the subject matter described herein. The method 800 is described with reference to the system 100 of FIG. 1.

Referring to FIG. 8, at block 802, the first part 304 of the longitudinal channel 208 is aligned with the first row 132 of the first set 126 of multiple rows of magnets. The alignment can be done by moving the magnetic arrangement 122 relative to the capture chip 104. The alignment causes the first part 304 of the longitudinal channel 300 to come under the influence of a magnetic field of magnets of the first row 132.

At block 804, the liquid sample is passed across the longitudinal channel 208 from the capture chip inlet 118 to the capture chip outlet 120. As mentioned earlier, the liquid sample has rare cells that are conjugated at least with magnetic particles. The presence of these magnetic particles on the rare cells causes the conjugated rare cells to get settled along the first part 304 of the longitudinal channel 208 due to the magnetic field.

At block 806, the wash buffer is passed across the longitudinal channel 208. As one may recall, this passage of wash buffer across the longitudinal channel 208 to wash away the non-specifically bound particles, i.e., the unbound particles, along the longitudinal channel.

At block 808, the first part 304 of the longitudinal channel 208 is aligned with a subsequent row of the first set 126, and, after the alignment, the wash buffer is passed across the longitudinal channel 208. Since the subsequent row has one less magnet than the previous row, the first part 304 is under the influence of magnetic field of one less magnet with respect to that for the previous alignment. The magnetic arrangement 122 is such that the first part 304 is under the influence of magnetic field of one less magnet from the capture chip inlet 118 in the subsequent alignment. With the passing of the wash liquid, the settled rare cells in the first part are swept towards the capture well 302 due to flowing of wash liquid and due to a gradient magnetic field being applied on the first part 304 of the longitudinal channel 208 through sequential alignment with the first set 126 of multiple rows of magnets.

At block 810, it is checked whether the subsequent row of the first set 126 aligned with the first part 304 of the longitudinal channel is the last row of the first set 126. If the subsequent row is not the last row of the first set 126 ('No' branch from block 810), then the step mentioned at block 808 is repeated, i.e., the first part 304 of the longitudinal channel 208 is aligned with a next row of the first set 126, and, after the alignment, the wash buffer is passed across the longitudinal channel 208.

If the subsequent row is the last row of the first set 126 ('Yes' branch from block 810), the capture well 302 of the longitudinal channel 208 is aligned with the isolated capture magnet 130 at block 812. The cross-sectional dimensions of the isolated capture magnet 130 is substantially similar to the coverage area of the capture well 302. When the capture well 302 is aligned with the isolated capture magnet 130, the capture well 302 comes under the influence of the magnetic field of the isolated capture magnet 130. It may be noted that at this stage, no other region of the longitudinal channel 208, except the capture well 302, is under the influence of a magnetic field. Also, the conjugated rare cells which were settled across the longitudinal channel 208 due to the magnetic field are now free to move due to the absence of any magnetic field.

At block 814, the wash buffer is made to flow across the longitudinal channel 208. With this, the wash buffer sweeps the conjugated rare cells into the capture well 302.

Although the present subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter.

We claim:

1. A system for magnetic capturing of rare cells from a liquid sample, wherein the rare cells are conjugated with magnetic particles through a binding agent, wherein the system comprises:
    a capture chip comprising:
        a longitudinal channel for passing the liquid sample, wherein the longitudinal channel has a first part and a second part interfaced with the first part, wherein the second part has a narrower cross-sectional width than the first part; and
        a capture well for the magnetic capturing of the rare cells from the passed liquid sample, wherein the capture well is near an end of the second part closer to an interfacing region between the first part and the second part; and
    a first set of multiple rows of magnets for the magnetic capturing of the rare cells in the first part of the longitudinal channel, wherein a first row of the first set of multiple rows has magnets that span a length of the first part of the longitudinal channel and each subsequent row of the first set of multiple rows has one magnet less than a previous row.

2. The system as claimed in claim 1, wherein the system comprises:
    a second set of multiple rows of magnets for the magnetic capturing of the rare cells in the capture well, wherein each row of the second set of multiple rows at least has a capture magnet having a cross-sectional area substantially equal to a coverage area of the capture well, and wherein rows of the second set of multiple rows are appended to predefined last rows of the first set of multiple rows of magnets from an end away from the first row of the first set of multiple rows of magnets; and
    an isolated capture magnet having a cross-sectional area substantially equal to the coverage area of the capture well.

3. The system as claimed in claim 1, wherein the capture chip comprises:
    a first layer comprising the longitudinal channel;
    a second layer coupled to the first layer to cover the longitudinal channel, wherein the second layer has a through-hole; and
    a third layer coupled to the second layer to cover the through-hole to form the capture well.

4. The system as claimed in claim 2, wherein the system comprises a linear positioner for moving the first set of multiple rows of magnets, the second set of multiple rows of magnets, and the isolated capture magnet with respect to the capture chip to,
    align the first part of the longitudinal channel with one row of the first set of multiple rows for passing of one of a liquid sample and a wash liquid through the longitudinal channel, wherein the capture well is aligned with the capture magnet of a row of the second set when the longitudinal channel is aligned with one of the predefined last rows of the first set; and
    align the longitudinal channel with the isolated capture magnet for passing the wash liquid for magnetic capturing of rare cells in the capture well.

5. The system as claimed in claim 3, wherein the first layer is made of a polydimethyl siloxane, the second layer is made of one of parafilm M and polypropylene, and the third layer is glass coverslide.

6. The system as claimed in claim 3, wherein the predefined thickness of the second layer is about 100 μm.

7. The system as claimed in claim 1, wherein the capture well has a cross-sectional diameter of about 2 mm.

8. The system as claimed in claim 1, wherein the first part of the longitudinal channel has a cross-sectional width of about 4 mm.

9. The system as claimed in claim 1, wherein the polarities of each pair of adjacent magnets in each row of the first set of multiple rows are opposite.

10. The system as claimed in claim 2, wherein the capture magnet in the each row of the second set of multiple rows has a cross-sectional width of about 2 mm.

11. The system as claimed in claim 1, wherein the magnets in the first set of multiple rows have cross-sectional width at least equal to a cross-sectional width of the first part of the longitudinal channel.

12. The system as claimed in claim 1, wherein the longitudinal channel comprises at least two sub-channels, wherein adjacent sub-channels of the at least two sub channels are separated by a polydimethyl siloxane (PDMS) block.

13. The system as claimed in claim 12, wherein each sub-channel of the at least two sub-channels has a cross-sectional width of about 4 mm.

14. The system as claimed in claim 12, wherein the PDMS block has a width of about 2 mm.

15. The system as claimed in claim 2, wherein the isolated capture magnet has a cross-sectional diameter of about 2 mm.

16. A method for magnetic capturing of rare cells from a liquid sample, wherein the rare cells are conjugated with magnetic particles through a binding agent, wherein the rare cells are captured in a capture well of a capture chip, wherein the capture chip has a longitudinal channel comprising a first part and the second part interfaced with the first part, the second part having a narrower cross-sectional width than the first part, and the capture well being located near an end of the second part closer to an interfacing region between the first part and the second part, wherein the method comprises:
    aligning the first part of the longitudinal channel with a first row of a first set of multiple rows of magnets, wherein the first row spans a length of the first part of the channel;
    passing the liquid sample across the longitudinal channel from a capture chip inlet at the first part to a capture chip outlet at the second part;
    passing a wash buffer across the longitudinal channel from the capture chip inlet to the capture chip outlet;
    aligning the first part of the longitudinal channel with subsequent rows of the first set of multiple rows of magnets, wherein each subsequent row has one magnet less than a previous row, and passing the wash buffer from the capture chip inlet to the capture chip outlet after each alignment with the each subsequent row; and wherein the aligning the longitudinal channel with one of predefined last rows of the first set comprises aligning the capture well with a capture magnet of a second set of multiple rows of magnets for the magnetic capturing of the rare cells in the capture well, wherein the capture magnet of the second set of multiple rows has a cross-sectional area substantially equal to a coverage area of the capture well.

17. The method as claimed in claim 16, wherein the method comprises:

after the aligning the longitudinal channel with a last row of the first set of multiple rows and the passing of the wash buffer, aligning the capture well with an isolated capture magnet, wherein the isolated capture magnet has a cross-sectional area substantially equal to the coverage area of the capture well; and passing the wash buffer from the capture chip inlet to the capture chip outlet.

* * * * *